US011738210B2

(12) United States Patent
Wang et al.

(10) Patent No.: US 11,738,210 B2
(45) Date of Patent: Aug. 29, 2023

(54) MEDICAL SYSTEMS AND METHODS

(71) Applicant: SHANGHAI UNITED IMAGING HEALTHCARE CO., LTD., Shanghai (CN)

(72) Inventors: Yifeng Wang, Shanghai (CN); Yige Zhang, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 342 days.

(21) Appl. No.: 17/024,768

(22) Filed: Sep. 18, 2020

(65) Prior Publication Data
US 2021/0077828 A1 Mar. 18, 2021

(30) Foreign Application Priority Data
Sep. 18, 2019 (CN) .......................... 201910879552.7

(51) Int. Cl.
A61B 6/03 (2006.01)
A61N 5/10 (2006.01)

(52) U.S. Cl.
CPC .............. A61N 5/1049 (2013.01); A61B 6/03 (2013.01); A61N 5/1077 (2013.01); A61N 2005/1052 (2013.01); A61N 2005/1055 (2013.01); A61N 2005/1058 (2013.01); A61N 2005/1061 (2013.01)

(58) Field of Classification Search
CPC ........... A61B 6/03; A61B 6/032; A61B 6/102; A61B 6/44; A61B 6/4411; A61B 6/4417; A61B 6/4447; A61B 6/54; A61N 2005/1052; A61N 2005/1055; A61N 2005/1058; A61N 2005/1061; A61N 5/1049; A61N 5/1077; A61N 5/1081
See application file for complete search history.

(56) References Cited

U.S. PATENT DOCUMENTS

| 2004/0024300 | A1* | 2/2004 | Graf | ..................... A61N 5/1049 600/407 |
| 2005/0267348 | A1* | 12/2005 | Wollenweber | ......... A61B 6/544 600/407 |
| 2006/0113482 | A1* | 6/2006 | Pelizzari | ............... G01T 1/1641 250/370.09 |
| 2007/0025513 | A1* | 2/2007 | Ghelmansarai | ....... G01T 1/2018 378/98.8 |

(Continued)

FOREIGN PATENT DOCUMENTS

| CN | 104000617 A | 8/2014 |
| CN | 104656367 A | 9/2014 |

(Continued)

Primary Examiner — Thaddeus B Cox
Assistant Examiner — Marc D. Honrath
(74) Attorney, Agent, or Firm — METIS IP LLC

(57) ABSTRACT

Medical systems and methods are provided in the present disclosure. The medical system may include a first medical device mounted on a first gantry. The first medical device may be configured to perform a first operation on a first region of an object. The medical system may also include a second medical device mounted on a second gantry. The second medical device may be configured to perform a second operation on a second region of the object. The second gantry may rotate relative to the first gantry. The first region may at least partially overlap the second region.

20 Claims, 12 Drawing Sheets

(56) References Cited

U.S. PATENT DOCUMENTS

| | | | |
|---|---|---|---|
| 2011/0080990 A1* | 4/2011 | Filiberti | G16H 20/40 |
| | | | 378/65 |
| 2012/0035470 A1* | 2/2012 | Kuduvalli | A61B 6/00 |
| | | | 600/427 |
| 2012/0230464 A1 | 9/2012 | Ling et al. | |
| 2013/0234710 A1 | 9/2013 | Kanno et al. | |
| 2017/0258426 A1* | 9/2017 | Risher-Kelly | A61B 6/12 |
| 2019/0090829 A1* | 3/2019 | Gao | A61B 6/4014 |
| 2019/0150865 A1* | 5/2019 | Johnson | A61B 6/547 |
| 2019/0209868 A1 | 7/2019 | Stahl et al. | |
| 2019/0274649 A1 | 9/2019 | Fahrig et al. | |
| 2019/0366125 A1* | 12/2019 | Petterson | A61B 6/03 |
| 2020/0016432 A1* | 1/2020 | Maolinbay | A61N 5/1047 |

FOREIGN PATENT DOCUMENTS

| | | |
|---|---|---|
| CN | 107773853 A | 3/2018 |
| WO | 2018183748 A1 | 10/2018 |

* cited by examiner

1000

Causing a second gantry on which a second medical device is mounted rotates relative to a first gantry on which a first medical device is mounted — 1010

Causing the first medical device to perform a first operation and the second medical device to perform a second operation synchronously — 1020

FIG. 10

MEDICAL SYSTEMS AND METHODS

CROSS-REFERENCE TO RELATED APPLICATIONS

This application claims priority of Chinese Patent Application No. 201910879552.7, filed on Sep. 18, 2019, the contents of which are hereby incorporated by reference.

TECHNICAL FIELD

The present disclosure generally relates to medical technology, and more particularly, medical systems and methods for using the same.

BACKGROUND

In modern medicine, multiple types medical devices emitting radiation beams are used for medical imaging or treatment. For example, an imaging device (e.g., a computed tomography (CT) device, a cone-beam CT (CBCT) device, or an X-ray imaging device) may perform an imaging operation on a subject (e.g., a patient or a portion thereof) using radiation beams. As another example, a treatment device (e.g., a radiation therapy (RT) device such as a linear accelerator) may perform a treatment operation on a subject using radiation beams.

SUMMARY

In an aspect of the present disclosure, a medical system is provided. The medical system may include a first medical device mounted on a first gantry. The first medical device may be configured to perform a first operation on a first region of an object. The medical system may also include a second medical device mounted on a second gantry. The second medical device may be configured to perform a second operation on a second region of the object. The second gantry may rotate relative to the first gantry. The first region may at least partially overlap the second region.

In some embodiments, the first medical device may be imaging device, and the first operation may include imaging operation.

In some embodiments, the second medical device may be treatment device, and the second operation may include treatment operation.

In some embodiments, the treatment device may be linear accelerator.

In some embodiments, the second medical device may be second imaging device, and the second operation may include second imaging operation.

In some embodiments, the second gantry may be second ring gantry, and at least a portion of the second gantry may be located within a first bore defined by the first gantry.

In some embodiments, the second gantry may rotate around a central axis of the second gantry or a diameter of the second gantry.

In some embodiments, the first gantry may be ring gantry, and at least a portion of the first gantry may be located within a second bore defined by the second gantry.

In some embodiments, the first gantry may rotate relative to the second gantry. The first gantry may rotate around a central axis of the first gantry or a diameter of the first gantry.

In some embodiments, the first gantry may be movably connected to the second gantry.

In some embodiments, the first gantry and the second gantry may be concentric. An isocenter of the first gantry may coincide with an isocenter of the second gantry.

In some embodiments, the first gantry and the second gantry may be coaxial. The first gantry may share a same axis with the second gantry.

In some embodiments, at least a portion of the first gantry may be configured to be positioned within a second bore defined by the second gantry by rotating the first gantry.

In some embodiments, the medical system may further include a third medical device mounted on a third gantry. The third medical device may be configured to perform a third operation on a third region of the object. The third gantry may rotate relative to the second gantry. The third region may at least partially overlap the second region.

In some embodiments, the third medical device may be third imaging device, and the third operation may include third imaging operation.

In some embodiments, the first region, the second region, and the third region may share a same overlapped region.

In some embodiments, the medical system may further include a support on which the second gantry is mounted. The second gantry may rotate relative to the support.

In another aspect of the present disclosure, a method for using a medical system including a first medical device and a second medical device is provided. The method may be implemented on a computing device including at least one processor and at least one storage device. The first medical device may be configured to perform a first operation on a first region of an object and the second medical device may be configured to perform a second operation on a second region of the object. The method may include causing a second gantry on which the second medical device is mounted to rotate relative to a first gantry on which the first medical device is mounted such that the second region may at least partially overlap the first region. The method may also include causing the first medical device to perform the first operation and the second medical device to perform the second operation synchronously.

In some embodiments, the first medical device may be imaging device and the second medical device may be treatment device.

In some embodiments, the first medical device may be imaging device and the second medical device may be second imaging device.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 10 is a flowchart illustrating an exemplary process for using a medical system according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different levels in ascending order. However, the terms may be displaced by other expression if they achieve the same purpose.

Figure 7:
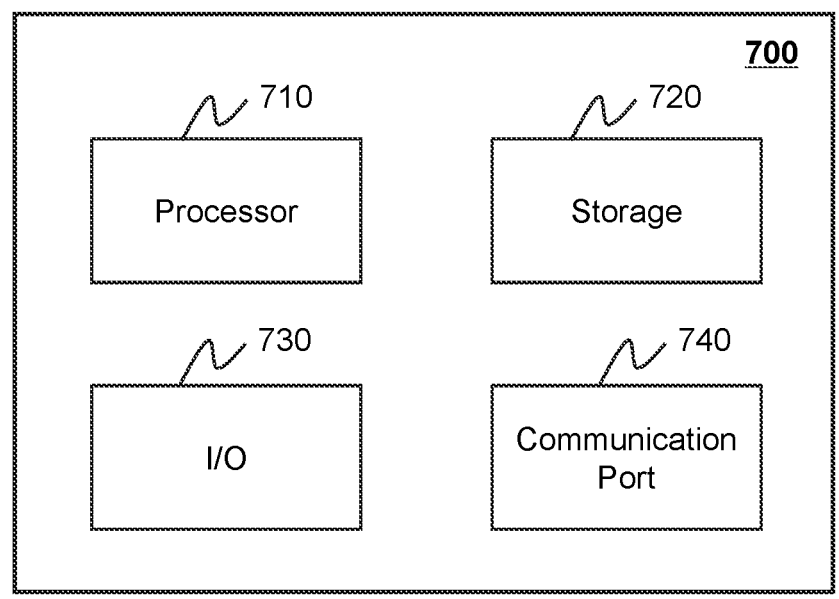
FIG. 7 is a schematic diagram illustrating exemplary hardware and/or software components of a computing device on which the processing device 120 may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 710 as illustrated in FIG. 7) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding a process for exposure controlling. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

The term "imaging modality" or "modality" as used herein broadly refers to an imaging method or technology that gathers, generates, processes, and/or analyzes imaging information of an object. The object may include a biological object (e.g., a human, an animal), a non-biological object (e.g., a phantom), etc. In some embodiments, the object may include a specific part, organ, and/or tissue of the object. For example, the object may include head, brain, neck, body, shoulder, arm, thorax, cardiac, stomach, blood vessel, soft tissue, knee, feet, or the like, or any combination thereof. The term "object" or "subject" are used interchangeably.

In this present disclosure, the terms "radiation therapy," "radiotherapy," "radiation treatment," and "treatment" may be used interchangeably to refer to a therapy for treating, e.g., cancers and other ailments in biological (e.g., human and animal) tissue using radiation. The terms "treatment plan," "therapy plan," and "radiotherapy plan" may be used interchangeably to refer to a plan used to perform radiotherapy.

Medical devices of different modalities may need to be used in combination to achieve better imaging and/or treatment purposes (e.g., multi-modality imaging or image guided radiation therapy (IGRT)). Currently, a subject may need to be moved among different examination rooms where the medical devices are located or be moved among different positions in an examination room where the medical devices are located. Thus, it is desirable to provide an effective medical system and method for using the medical system, in which the medical devices can perform imaging/treatment operations when the subject is located at a same position, thereby avoiding transportation and repeated positioning of the subject in different medical devices, which in turn may improve efficiency and accuracy of imaging and/or treatment of the subject.

The present disclosure provides a solution to an imaging/treatment of a subject using at least a first medical device and a second medical device. The first medical device may be configured to perform a first operation on a first region of the subject. The second medical device may be configured to perform a second operation on a second region of the subject. In some embodiments, the first medical device may be mounted on a first gantry. The second medical device may be mounted on a second gantry. The second gantry may rotate relative to the first gantry. The first region may at least partially overlap the second region. For example, the first medical device may include an imaging device and the second medical device may include a treatment device. The subject may receive a treatment beam from the second device and receive an imaging beam from the first device when the subject is maintained at a same position. The subject may be imaged by the first medical device before, when, or during the treatment, to, e.g., provide information of the subject during the treatment and/or guide the treatment of the subject. Alternatively, both the first medical device and the second device may include imaging devices. The subject may undergo imaging by the first medical device and the second medical device of different modalities, respectively, when the subject is maintained at the same position. The subject may be imaged by the first medical device and the second medical device to obtain different anatomical and/or metabolic information of the subject.

The medical systems and methods for using the medical systems as disclosed herein provide a cost-efficient and time-efficient solution to be used in imaging/treatment using different medical devices. The subject may be imaged and/or treated at the same position without being moved between the different medical devices, thereby improving the efficiency and/or accuracy of the imaging/treatment of the subject. Taking an image guided radiation therapy (IGRT) system as an example, the IGRT system may include an imaging device (e.g., a CT device) and a treatment device (e.g., a linear accelerator (Linac)). The CT device may be mounted on a first gantry and the Linac may be mounted on a second gantry. In some embodiments, the subject may be imaged during the treatment of the subject to accurately position a target volume of the subject that needs radiotherapy. For example, scan positions and angles of the CT device may be flexibly adjusted by rotating the first gantry to obtain an image or position information of the target volume of the subject for guiding the treatment of the subject. As another example, radiation delivery of the Linac may be flexibly adjusted by rotating the second gantry to better target the treatment radiation at the target volume and avoid an organ or tissue in the vicinity of the target volume from being radiated by the Linac. Moreover, a relative position between the CT device and the Linac may be flexibly adjusted by, e.g., rotating the first gantry and/or the second gantry, which can reduce or avoid the interference between the CT device and the Linac. Furthermore, the setting of two gantries as disclosed herein may integrate the CT device and the Linac as two components of a medical device such that the structure of the medical system may be simplified and conveniently installed.

Figure 1:
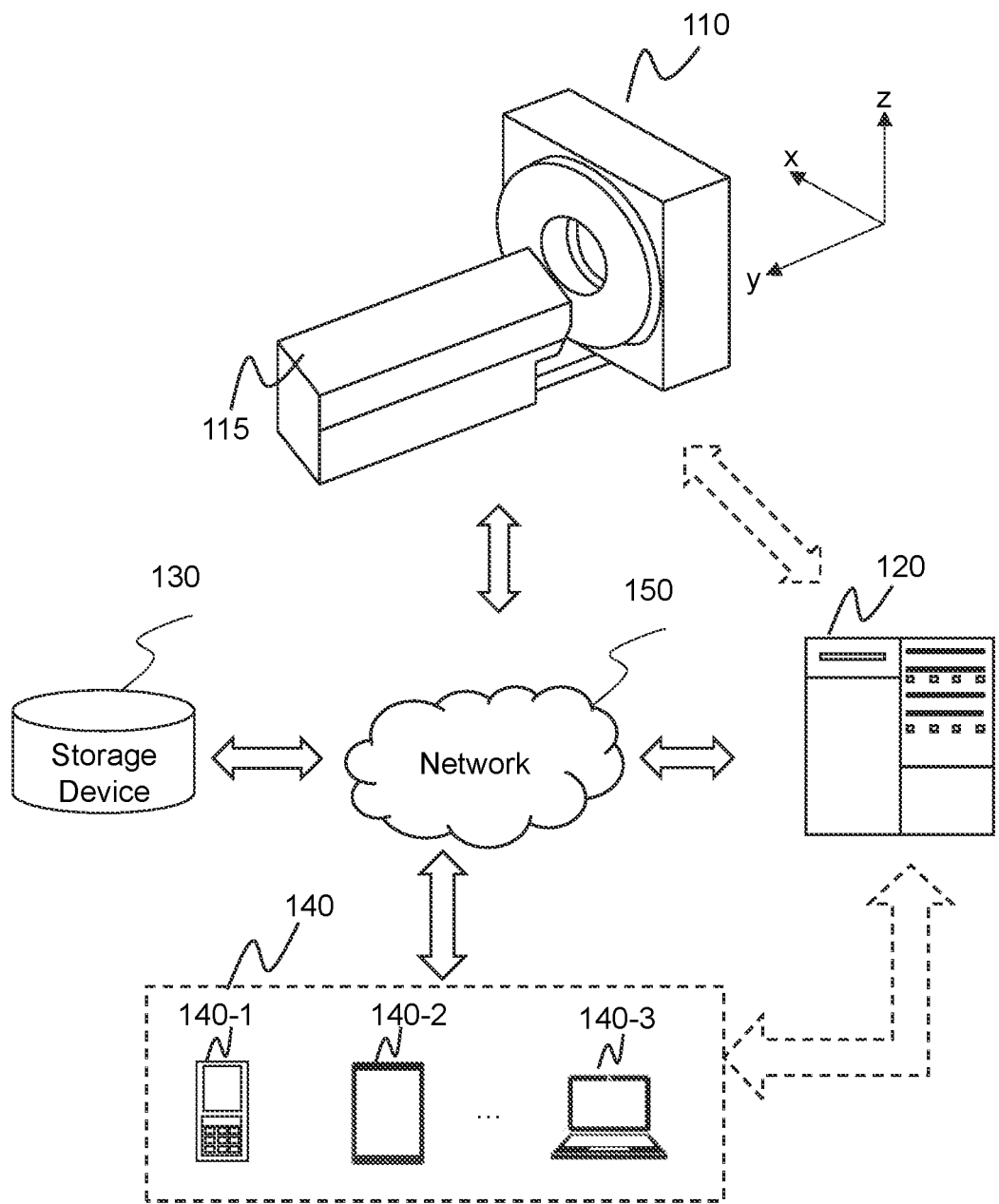
FIG. 1 is a schematic diagram illustrating an exemplary medical system according to some embodiments of the present disclosure.

FIG. 1 is a schematic diagram illustrating an exemplary medical radiation system according to some embodiments of the present disclosure. In some embodiments, the medical radiation system 100 may be configured to provide radiation imaging and/or radiation therapy of an object, or a portion thereof. In the present disclosure, "subject" and "object" are used interchangeably, unless expressly stated otherwise. In some embodiments, the medical radiation system 100 may include a multi-modality imaging system, an image-guided radiotherapy (IGRT) system, etc. The multi-modality imaging system may be configured to perform imaging operations on an object using different imaging devices, which can provide comprehensive anatomical information of the object. The multi-modality imaging system may include, for example, a computed tomography and cone-beam computed tomography (CT-CBCT) system, a CT and X-ray imaging (CT-X-ray) system, a positron emission tomography and X-ray imaging (PET-X-ray) system, a magnetic resonance imaging and CT (MRI-CT) system, etc. The IGRT system may be configured to perform radiation therapy on the object under the guidance of imaging the object, which can accurately position a target volume to be treated inside the object. The IGRT system may include, for example, a CT guided radiotherapy system, a CBCT guided radiotherapy system, an X-ray guided radiotherapy system, an MRI guided radiotherapy system, etc. It should be noted that the medical radiation system 100 (also referred to as a medical system 100 for brevity) being an IGRT system described below is merely provided for illustration purposes, and not intended to limit the scope of the present disclosure.

As illustrated in FIG. 1, the medical radiation system 100 may include a radiation device 110, a processing device 120, a storage device 130, one or more terminals 140, and a network 150. The components in the medical radiation system 100 may be connected in one or more of various ways. Merely by way of example, the radiation device 110 may be connected to the processing device 120 through the network 150. As another example, the radiation device 110 may be connected to the processing device 120 directly as indicated by the bi-directional arrow in dotted lines linking the radiation device 110 and the processing device 120. As a further example, the storage device 130 may be connected to the processing device 120 directly or through the network 150. As still a further example, the terminal 140 may be connected to the processing device 120 directly (as indicated by the bi-directional arrow in dotted lines linking the terminal 140 and the processing device 120) or through the network 150.

In some embodiments, the medical radiation system 100 may perform image guided radiation therapy (IGRT) that monitors, using X-ray imaging, a target volume (e.g., a tumor, a lesion, etc.) to be treated inside an object (e.g., a patient). In this case, the radiation device 110 may include an imaging device (also referred to as an imaging assembly), a treatment device (also referred to as a treatment assembly), and a table 115. The table 115 may be configured to support and move the object to a target position for imaging/ treatment. The treatment device may be configured to deliver a treatment beam to the target volume to perform radiotherapy on the target volume. The imaging device may be configured to perform imaging (e.g., two-dimensional (2D) imaging, three-dimensional (3D) imaging, or four-dimensional (4D) imaging) on the target volume and/or normal tissue surrounding the target volume (also referred to as "organ at risk") before, after, or while the radiotherapy is performed. In this way, the anatomy, as well as the motion or deformation, of the target volume can be detected, and the patient's position and/or the treatment beam can be adjusted for more precise radiation dose delivery to the target volume.

In some embodiments, the imaging device may include a non-invasive imaging device such as a CT device, a CBCT device, an X-ray device, a PET device, an MRI device, etc. Taking the CT device as an example, the imaging device may include a radiation source, a detector, etc. The radiation source may be configured to emit radioactive rays (e.g., X-rays) traveling toward the object. The detector may detect radiation (e.g., X-rays) emitted from the imaging region of the imaging device. In some embodiments, the detector may include one or more detector units. The detector unit(s) may include a scintillation detector (e.g., a cesium iodide detector, a gadolinium oxysulfide detector), a gas detector, etc. The detector unit(s) may include a single-row detector and/or a multi-rows detector. In some embodiments, the treatment device may include a treatment head. The treatment head may include a linear accelerator (Linac), a cyclotron, a synchrotron, etc. Taking the Linac as an example, the Linac may include an accelerator of species of particles for radiotherapy to malignant tumors. The Linac may be configured to emit a treatment beam, for example, an X-rays, a photon beam, an electron beam, a proton beams, a heavy ion beam, etc., toward the object for treatment. In some embodiments, the treatment beam may include a relatively high energy beam (e.g., an MV beam). In some embodiments, the treatment beam may include a fan beam, a cone beam, or a tetrahedron beam. Details regarding the radiation device 110 can be found elsewhere in the present disclosure (e.g., descriptions in connection with FIGS. 2-6).

In the present disclosure, the x axis, the y axis, and the z axis shown in FIG. 1 may form an orthogonal coordinate system. The x axis and the y axis shown in FIG. 1 may be horizontal, and the z axis may be vertical. As illustrated, the positive x direction along the x axis may be from the right side to the left side of the radiation device 110 seen from the direction facing the front of the radiation device 110; the positive z direction along the z axis shown in FIG. 1 may be from the lower part to the upper part of the radiation device 110; the positive y-direction along the y axis shown in FIG. 1 may refer to a direction in which an object is moved out of a bore of the radiation device 110.

In some embodiments, the processing device 120 may process data obtained from the radiation device 110, the terminal 140, or the storage device 130. For example, the processing device 120 may obtain projection data of an object from the radiation device 110 and generate an image of the object based on the projection data. As another example, the processing device 120 may cause one or more components (e.g., a treatment head, an imaging radiation source, a detector, a collimator, a patient supporter, a gantry, etc.) of the radiation device 110 to be located at a specific position. The processing device 120 may be a central processing unit (CPU), a digital signal processor (DSP), a system on a chip (SoC), a microcontroller unit (MCU), or the like, or any combination thereof.

In some embodiments, the processing device 120 may be a single server or a server group. The server group may be centralized or distributed. In some embodiments, the processing device 120 may be local or remote. For example, the processing device 120 may access information and/or data stored in the radiation device 110, the terminal 140, and/or the storage device 130 via the network 150. As another example, the processing device 120 may be directly connected to the radiation device 110, the terminal 140, and/or the storage device 130, to access stored information and/or data. In some embodiments, the processing device 120 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 130 may store data and/or instructions. In some embodiments, the storage device 130 may store data obtained from the terminal 140 and/or the processing device 120. For example, the storage device 130 may store one or more images generated by the processing device 120. In some embodiments, the storage device 130 may store data and/or instructions that the processing device 120 may execute or use to perform exemplary methods described in the present disclosure. For example, the storage device 130 may store instructions that the processing device 120 may execute or use to generate one or more images based on projection data. In some embodiments, the storage device 130 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 130 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 130 may be connected to the network 150 to communicate with one or more components of the medical radiation system 100 (e.g., the radiation device 110, the terminal 140, the processing device 120). One or more components of the medical radiation system 100 may access the data or instructions stored in the storage device 130 via the network 150. In some embodiments, the storage device 130 may be directly connected to or communicate with one or more components of the medical radiation system 100 (e.g., the terminal 140, the processing device 120). In some embodiments, the storage device 130 may be part of the processing device 120.

The terminal 140 may include a mobile device 140-1, a tablet computer 140-2, a laptop computer 140-3, or the like, or any combination thereof. In some embodiments, the mobile device 140-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the terminal 140 may remotely operate the radiation device 110. In some embodiments, the terminal 140 may operate the radiation device 110 via a wireless connection. In some embodiments, the terminal 140 may receive information and/or instructions inputted by a user, and send the received information and/or instructions to the radiation device 110 or to the processing device 120 via the network 150. In some embodiments, the terminal 140 may receive data and/or information from the processing device 120. In some embodiments, the terminal 140 may be part of the processing device 120. In some embodiments, the terminal 140 may be omitted.

The network 150 may facilitate exchange of information and/or data. In some embodiments, one or more components of the medical radiation system 100 (e.g., the radiation device 110, the terminal 140, the processing device 120, or the storage device 130) may send information and/or data to another component(s) in the medical radiation system 100 via the network 150. For example, the processing device 120 may obtain a user instruction from the terminal 140 via the network 150. As another example, the processing device 120 may obtain scan data (e.g., projection data) from the radiation device 110 via the network 150. In some embodiments, the network 150 may be any type of wired or wireless network, or combination thereof. The network 150 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 150 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, or the like, or any combination thereof. In some embodiments, the network 150 may include one or more network access points. For example, the network 150 may include wired or wireless network access points such as base stations and/or internet exchange points through which one or more components of the medical radiation system 100 may be connected to the network 150 to exchange data and/or information.

Figure 2:
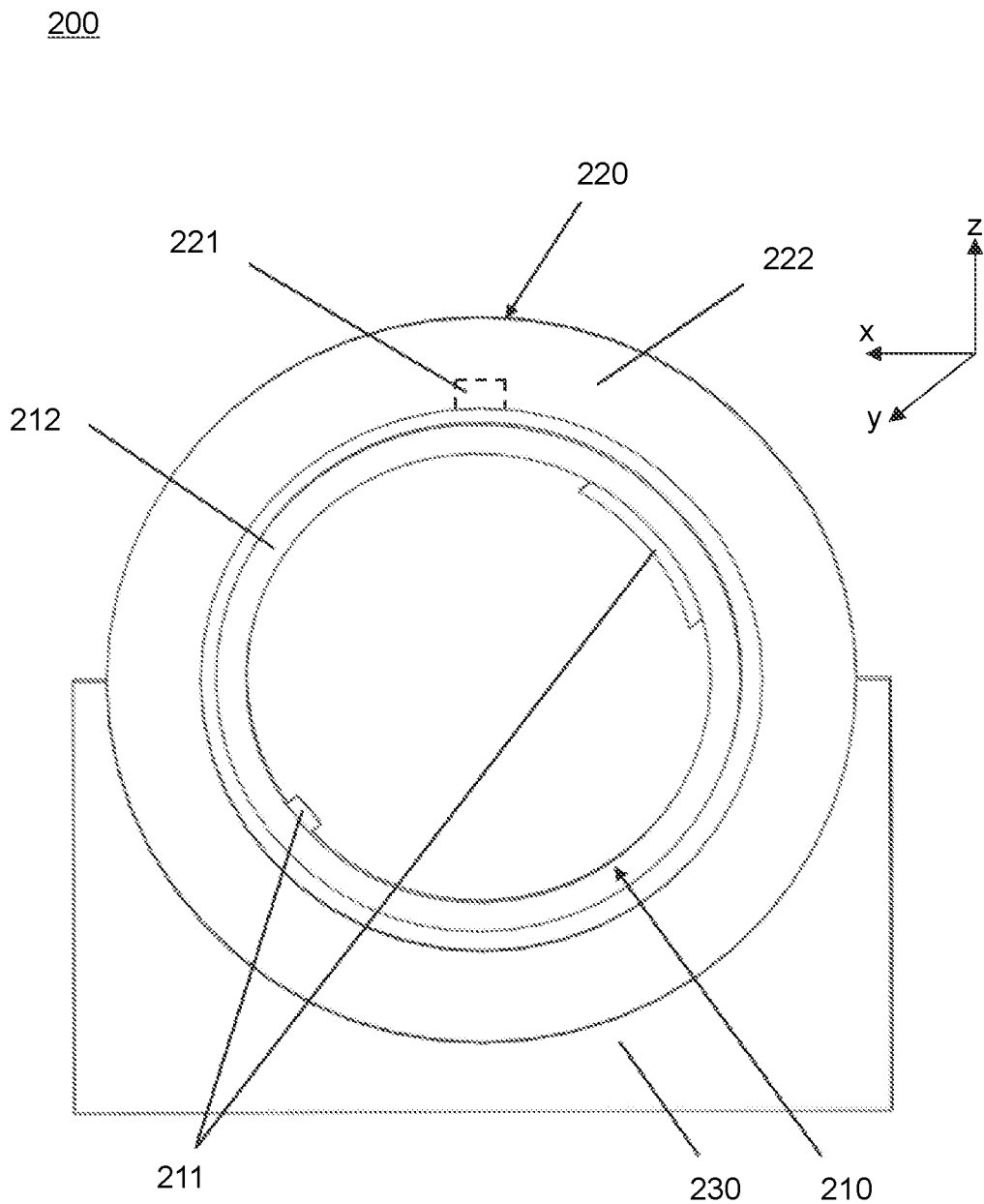
FIG. 2 is a schematic diagram illustrating an exemplary radiation device according to some embodiments of the present disclosure.

FIG. 2 is a schematic diagram illustrating an exemplary radiation device according to some embodiments of the present disclosure. The radiation device 200 provides an exemplary embodiment of the radiation device 110 as described in connection with FIG. 1. The radiation device 200 may include a first device 210, a second device 220, and a support 230. As shown in FIG. 2, the first device 210 and the second device 220 may be at their initial positions. The coordinate system illustrated in FIG. 2 may be the same as that illustrated in FIG. 1. For illustration purposes, the following descriptions of the radiation device 200 being an IGRT device may not be intended to limit the scope of the present disclosure.

The first device 210 may include a first medical device 211 and a first gantry 212. The first medical device 211 may be an imaging device (also referred to as a first imaging device) (e.g. a CT device, a CBCT device, an X-ray device, an MRI device, a PET device, etc.) similar to the imaging device as described in FIG. 1. The first medical device 211 may be configured to perform intrafractional imaging of an object (e.g., a patient or an animal) by emitting an imaging beam (e.g., an X-ray beam, a gamma (γ) beam, an ultrasonic wave, etc.) towards the object. Taking the CT device as an example, the first medical device 211 may include a radiation source which includes a tube and a detector. The first medical device 211 may be configured to perform a first operation (e.g., an imaging operation) on a first region of an object. The first region of the object may refer to a region of interest (ROI) of the object including at least a portion of a target volume to be treated inside the object and/or one or more organs at risk (OARs) of the object. The first region of the object may include a specific part or a specific organ or tissue of the object. For a patient, the first region may include the head, the chest, the abdomen, the esophagus, the trachea, a lung, the stomach, the liver, a kidney, the spleen, an intestine, the uterus, etc., of the patient.

The first gantry 212 may be configured to support at least one of components of the first medical device 211. The first medical device 211 (e.g., the radiation source and/or the detector of the first medical device 211) may be configured to be operably coupled to or mounted on the first gantry 212. For example, the first medical device 211 may be fixedly mounted on the first gantry 212 and move with the first gantry 212. As another example, the first medical device 211 may be movably mounted on the first gantry 212. The first medical device 211 may rotate relative to the first gantry 212. For instance, the first gantry 212 may include a first structure such as a rail, a sliding chute, or a slip ring on a wall (e.g., an inner wall or a surface wall) of the first gantry 212. The first medical device 211 may move along the first structure. In some embodiments, the first medical device 211 may be driven to rotate relative to the first gantry 212 by a driving device. For illustration purposes, the following description is provided in connection with the first medical device 211 fixedly mounted on the first gantry 212, which is not limiting.

In some embodiments, the first gantry 212 may rotate around the object that is moved into a field of view (FOV) (e.g., a region covered by the radiation beams emitted from the radiation source of the first medical device 211 and the second device 220) of the radiation device 200. For example, the first gantry 212 may rotate around a rotation axis parallel to the y-direction. As another example, the first gantry 212 may rotate relative to the second gantry 222. That is, the first gantry 212 may rotate around a rotation axis perpendicular to the y-direction. For instance, the first gantry 212 may rotate around two orthogonal axes (e.g., two perpendicular axes which are perpendicular to the y-direction), which is conducive to adjusting the scan position and/or angle of the first medical device 211 for obtaining an image of the target volume to be treated inside the object during a treatment session of the object. The scan angle refers to an angle between a vertical line (e.g., a line parallel to the z direction) and a line formed by the radiation source and the detector of the first medical device 211. As still another example, the first gantry 212 may rotate around a direction such as the clockwise direction or the anticlockwise direction. As further another example, the first gantry 212 may oscillate back and forth. In some embodiments, the first gantry 212 may include a ring gantry, a C-arm gantry, etc. As shown in FIG. 2, the first gantry 212 may be a ring gantry having a toroidal shape in which the patient's body extends through a bore (also referred to as a first bore) defined by the first gantry 212. In such cases, the first gantry 212 may be configured to rotate around a central axis (e.g., an axis passing through a center of the first bore and perpendicular to the first bore) of the first gantry 212 or around a diameter of the first gantry 212 (e.g., a diameter of the first bore).

The second device 220 may include a second medical device 221 and a second gantry 222. The second medical device 221 may be a treatment device including a treatment head such as a Linac. The second medical device 221 may be configured to perform a second operation (e.g., a treatment operation) on a second region of an object (e.g., a patient). The second region of the object may refer to a target volume to be treated inside the object. For example, the second region may include a tumor, a lesion, etc., of a patient. As another example, the second region may include a specific part or a specific organ or tissue of the object. For instance, the second region may include the head, the chest, the abdomen, the esophagus, the trachea, a lung, the stomach, the liver, a kidney, the spleen, an intestine, the uterus, etc., of the patient, which is similar to the first region. In some embodiments, the first region may at least partially overlap the second region. Merely by way of example, the first region may include the abdomen of a patient, and the second region may include a tumor inside the abdomen of the patient.

The second gantry 222 may be configured to support the second medical device 221. The second medical device 221 may be configured to be operably coupled to or mounted on the second gantry 222. For example, the second medical device 221 may be fixedly mounted on the second gantry 222. The second medical device 221 may move with the second gantry 222. As another example, the second medical device 221 may be movably mounted on the second gantry 222. The second medical device 221 may rotate relative to the second gantry 222. For instance, the second gantry 222 may include a second structure such as a rail, a sliding chute, or a slip ring on a wall (e.g., an inner wall or a surface wall) of the second gantry 222. The second medical device 221 may move along the second structure. In some embodiments, the second medical device 221 may be driven to rotate relative to the second gantry 222 by a driving device. For illustration purposes, the following description is provided in connection with the second medical device 221 fixedly mounted on the second gantry 222. In such cases, the second medical device 221 may be arranged to have relatively more radiation positions and angles as the second gantry 222 rotates.

In some embodiments, the second gantry 222 may rotate around the object that is moved into the FOV of the radiation device 200. That is, the imaging operation and the treatment operation may be performed on the object when the object is moved into the same position. For example, the second gantry 222 may rotate around a rotation axis parallel to the y-direction. As another example, the second gantry 222 may rotate relative to the first gantry 212. That is, the second gantry 222 may rotate around a rotation axis perpendicular to the y-direction. As still another example, the second gantry 222 may rotate along a direction such as the clockwise direction or the anticlockwise direction. As further another example, the second gantry 222 may oscillate back and forth. In some embodiments, the second gantry 222 may include a ring gantry, a C-arm gantry, etc. As shown in FIG. 2, the second gantry 222 may be a ring gantry having a toroidal shape which defines a second bore (e.g., a cylindrical accommodation space). Accordingly, the second gantry 222 may be configured to rotate around a central axis (e.g., an axis passing through a center of the second bore and perpendicular to the second bore) of the second gantry 222 or around a diameter of the second gantry 222 (e.g., a diameter of the second bore).

In some embodiments, at least a portion of the first gantry 212 may be configured to be positioned within the second bore defined by the second gantry 222. For example, when the first gantry 212 and the second gantry 222 are at their respective initial positions (e.g., the long axis of the first gantry 212 and the long axis of the second gantry 222 being parallel to they axis), the first gantry 212 may be positioned within the second bore defined by the second gantry 222. Alternatively, when the first gantry 212 rotates relative to the second gantry 222 or the second gantry 222 rotates relative to the first gantry 212, a first portion of the first gantry 212 may be outside the second bore and a second portion of the first gantry 212 may be kept within the second bore. See, e.g., FIGS. 3 and 4 and the description thereof. In such a design, the first gantry 212 and/or the second gantry 222 may be arranged compactly without collision with other components, which can reduce the volume of the radiation device 200.

Figure 3:
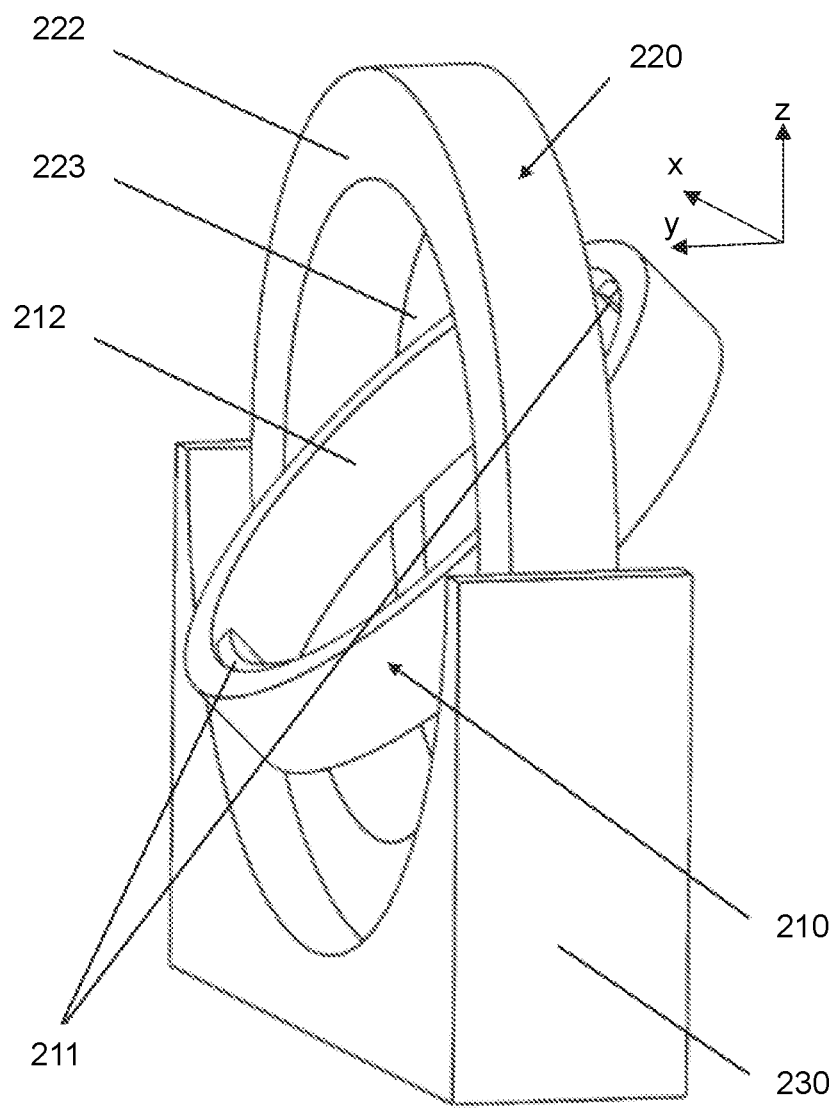
FIGS. 3 and 4 are schematic diagrams illustrating exemplary rotation states of the radiation device 200 according to some embodiment of the present disclosure.
Figure 4:
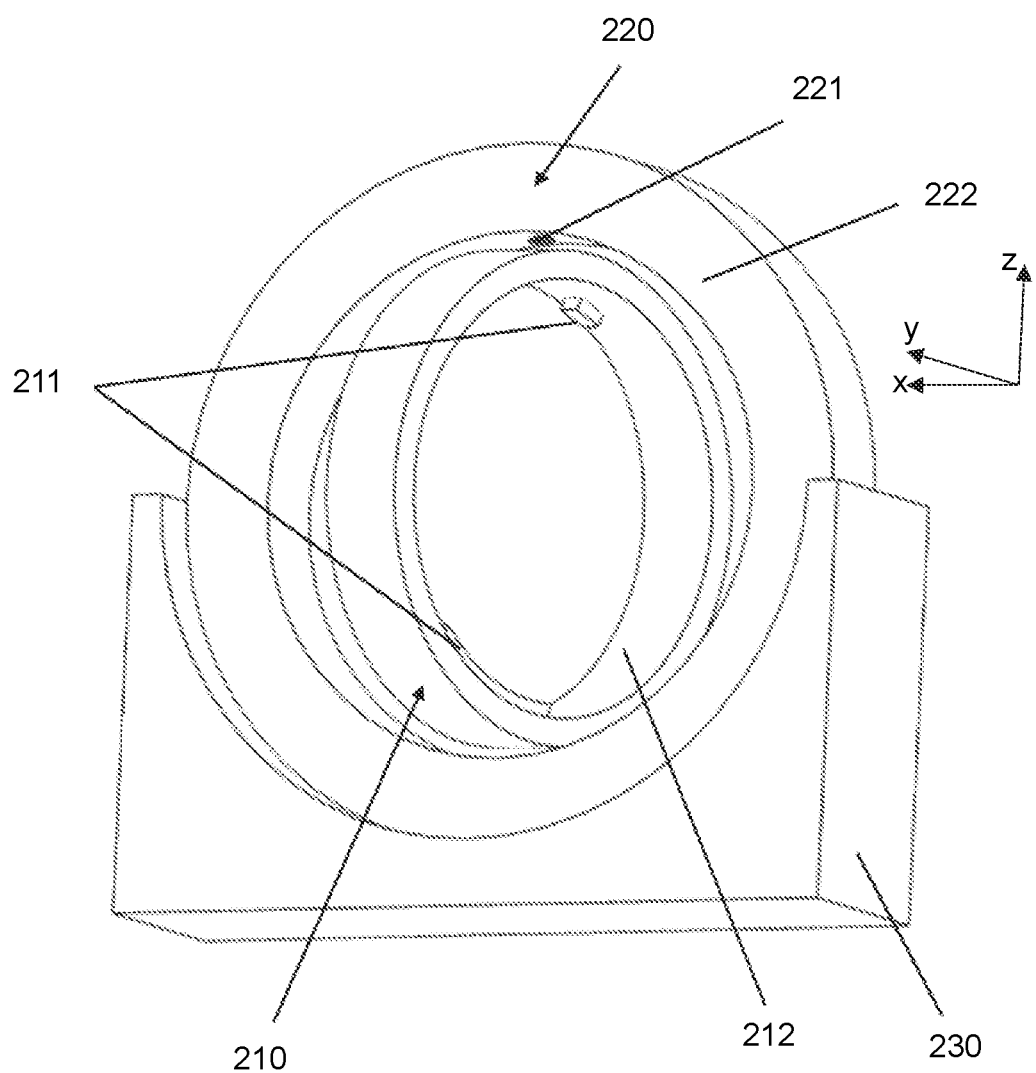

FIGS. 3 and 4 are schematic diagrams illustrating exemplary rotation states of the radiation device 200 according to some embodiment of the present disclosure. As shown in FIGS. 3 and 4, the second gantry 222 may define a cylindrical accommodation space (i.e., the second bore) 223. The cylindrical accommodation space 223 may include a central axis passing through the isocenter of the second medical device 221 and/or parallel to the y-direction. The first gantry 212 and/or the second gantry 222 may rotate around the central axis of the cylindrical accommodation space 223. In some embodiments, two ends of a diameter of the first gantry 212 may be operably mounted on the second gantry 222 by two joints. By the two joints, the first gantry 212 may rotate around not only the central axis of the cylindrical accommodation space 223 but also an axis parallel to the diameter of the first gantry 212. In such combination, the scan position and/or angle of the first medical device 211 may be adjusted more flexibly, thereby performing the imaging operation on the target volume inside the object more conveniently no matter where the target volume is positioned inside the object. As shown in FIG. 3, the first gantry 212 may rotate around an axis parallel to the x direction from its initial position to a first position. As shown in FIG. 4, the first gantry 212 may rotate around an axis parallel to the z-direction from its initial position to a second position.

In some embodiments, the first gantry 212 may be movably connected with the second gantry 222. That is, the first gantry 212 may be operably coupled to or mounted on the second gantry 222. For example, the first gantry 212 may be mounted on the second gantry 222 by a rotation support (not shown) (e.g., a ring support). The rotation support may be within the second bore when the first gantry 212 and the second gantry 222 are at their respective initial positions. The rotation support may include a first rotation axis (e.g., an axis parallel to the x direction) and a second rotation axis perpendicular to the first rotation axis (e.g., an axis parallel to the z direction). The first gantry 212 may be mounted on the rotation support such that the first gantry 212 may rotate with respect to the first rotation axis. The rotation support may be mounted on the second gantry 222 such that the rotation support may rotate with respect to the second rotation axis. Accordingly, the first gantry 212 may rotate relative to the second gantry 222 around the first rotation axis and/or second rotation axis. In some embodiments, a rotation angle of the first gantry 212 around a rotation axis (e.g., the first rotation axis, the second rotation axis, etc.) may be any angle without collision with other components (e.g., the second gantry 222, the object, the table, etc.) of the radiation device 200. For example, the rotation angle of the first gantry 212 around the first rotation axis or the second rotation axis may be within a range from 0° to 45°, e.g., 10°, 20°, 30°, etc. As another example, the rotation angle of the first gantry 212 around the first rotation axis or the second rotation axis may include 90°, 180°, 270°, or any other angles when the object has a relatively small size compared to the first bore defined by the first gantry 212.

In some embodiments, the first gantry 212 and the second gantry 222 may be concentric. That is, an isocenter of the first gantry 212 may coincide with an isocenter of the second gantry 222. As used herein, the isocenter of the first gantry 212 refers to a center point of a rotation plane within which the first medical device 211 rotates. The isocenter of the first gantry 212 may also be referred to as an isocenter of the first medical device 211 or a first isocenter. When the first gantry 212 is a ring gantry, the isocenter of the first gantry 212 may be a center point of the ring gantry. Similarly, the isocenter of the second gantry 222 refers to a center point of a rotation plane within which the second medical device 221 rotates. The isocenter of the second gantry 222 may also be referred to as an isocenter of the second medical device 221 or a second isocenter. When the second gantry 222 is a ring gantry, the second gantry 222 may define a cylindrical accommodation space. A center point of the cylindrical accommodation space may be the isocenter of the second gantry 222. In such a configuration, a center of the first region may coincide with a center of the second region, and an image obtained by scanning the object by the first medical device 211 may be directly used for guiding the radiotherapy of the target volume inside the object without correcting the image, thereby improving the accuracy of the positioning of the target volume using the first medical device 211. In some embodiments, the first isocenter may substantially coincide with the second isocenter. For example, when a distance or offset between the first isocenter and the second isocenter is within a threshold distance (e.g., 0.1 mm, 0.05 mm, etc.), the first isocenter may be regarded as substantially coinciding with the second isocenter.

The support 230 may be configured to support at least one of components of the radiation device 200 (e.g., the first gantry 212 the second gantry 222, etc.). Merely by way of example, the second gantry 222 may be movably connected with the support 230. That is, the second gantry 222 may be operably coupled to or mounted on the support 230 and rotate relative to the support 230. The second gantry 222 may rotate around a rotation axis perpendicular to the y-direction. For instance, the second gantry 222 may rotate around a third rotation axis parallel to the x-direction, a fourth rotation axis parallel to the z-direction, or the like, or any combination thereof. In some embodiments, the second gantry may rotate around two orthogonal axes relative to the support 230 (e.g., two perpendicular axes which are perpendicular to the y-direction), which is conducive to adjusting a radiation position and/or angle of the second medical device 221 more flexibly. The radiation angle refers to an angle between a vertical line (e.g., a line parallel to the z direction) and a line formed by the treatment head of the second medical device 221 and the isocenter of the second medical device 221. Accordingly, the accuracy of the radiation delivery by the second medical device 221 toward the target volume may be improved, and radiation of an organ or tissue in the vicinity of the target volume may be reduced or avoided. For example, when the target volume is located between the eyes of a patient, the second gantry 222 may rotate to a position where the second medical device 221 may radiate from above the head of the patient to the target volume to protect the eyes of the object from being radiated. In some embodiments, the second gantry 222 may be mounted on the support 230 on a second rotation support (e.g., not shown) (e.g., a second ring support). The second rotation support may include a third rotation axis (e.g., an axis parallel to the x direction) and a fourth rotation axis perpendicular to the third rotation axis (e.g., an axis parallel to the z direction). The second gantry 222 may be mounted on the second rotation support such that the second gantry 222 may rotate with respect to the third axis. The second rotation support may be mounted on the support 230 such that the second gantry 222 may rotate with respect to the fourth axis. Accordingly, the second gantry 222 may rotate relative to the support 230 around the third axis and/or fourth axis. In some embodiments, the second gantry 222 may rotate around its central axis on the support 230 such that the second medical device 221 may rotate around the central axis, thereby the second medical device 221 may traverse more radiation angles than a configuration that the second gantry 222 can not rotate around its central axis.

In some embodiments, a rotation angle of the second gantry 222 around an axis (e.g., the third axis, the fourth axis, etc.) may be any angle without collision with other components of the radiation device 200. For example, the rotation angle of the second gantry 222 around the third axis or the fourth axis may within a range from 0° to 45°, e.g., 10°, 20°, 30°, etc. As another example, the rotation angle of the second gantry 222 around the third axis or the fourth axis may include 90°, 180°, 270°, or any other angles when the object has a relatively small size with respect to the first bore defined by the first gantry 212. In some embodiments, the rotation angle range of the second gantry 222 and/or the first angle range of the first gantry 212 may be set by the medical radiation system 100 or a user (e.g., a doctor, a technician, etc.) of the medical radiation system 100. In some embodiments, the trajectory of the second medical device 221 may at least partially overlap the trajectory of the first medical device 211. In some embodiments, the trajectory of the second medical device 221 may be different from the trajectory of the first medical device 211. In some embodiments, the second medical device 221 and the first medical device 211 may rotate in a same plane or different planes.

Figure 12:
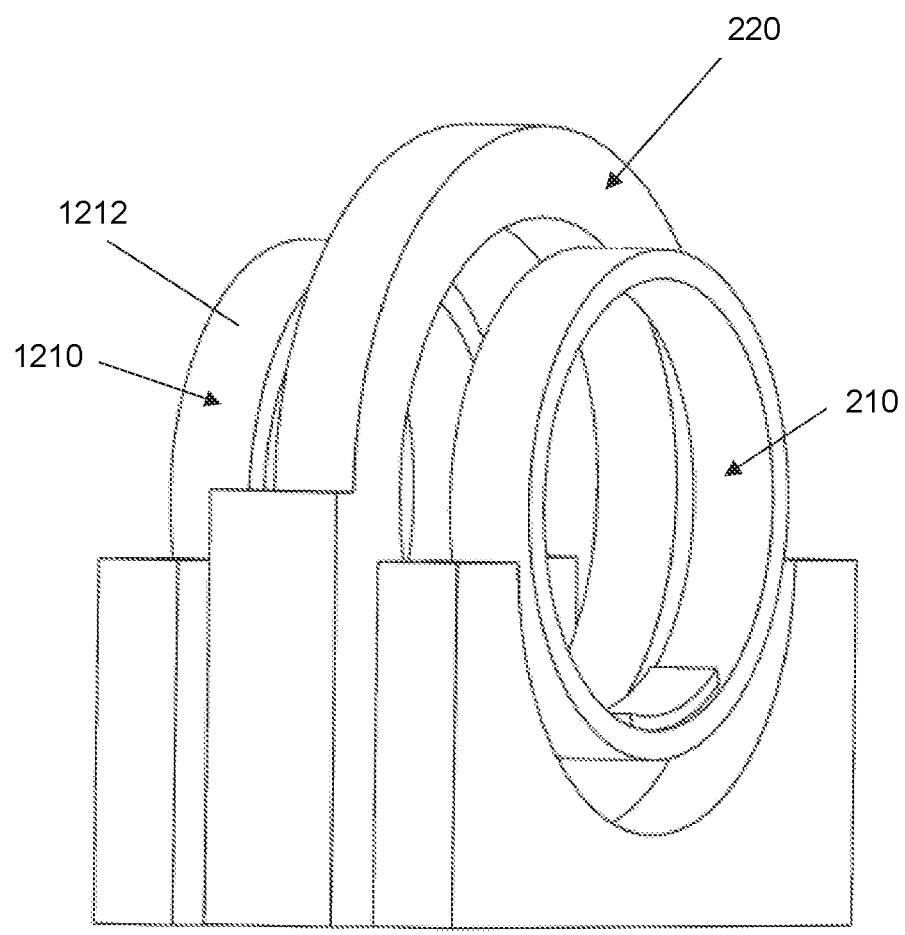
FIG. 12 is a schematic diagram illustrating an exemplary radiation device according to some embodiments of the present disclosure.

As shown in FIG. 12, in some embodiments, the radiation device 200 may further include a third device. The third device may include a third medical device 1210 and a third gantry 1212. The third medical device 1210 may be configured to perform a third operation on a third region of the object. The third medical device 1210 may include an imaging device or a treatment device. Taking the third device being an imaging device as an example, the third operation may include a third imaging operation. The third region may at least partially overlap the second region. In some embodiments, the third medical device 1210 may be of a same type as or of different types from the first medical device 211. For example, the third medical device 1210 and the first medical device 211 may both be a CT device, an X-ray imaging device, etc. In such a configuration, radiation beams emitted from the third medical device 1210 and the first medical device 211 may include different scan angles such that a user can select at least one from the third medical device 1210 and the first medical device 211 for the imaging of the object, thereby achieving a better imaging effect. As another example, the third medical device 1210 may include an MRI device and the first medical device 211 including a CT device. Alternatively, the third medical device 1210 may include an X-ray imaging device, and the first medical device 211 may include a PET device. In such a configuration, images with different types generated by the first medical device 211 and the third medical device 1210 may be used to guide the second medical device 221 to perform the treatment operation on the target volume inside the object during the radiotherapy of the object, thereby improving the accuracy of the positioning of the target volume. In some embodiments, the first region, the second region, and the third region may at least partially overlap. That is, the first region, the second region, and the third region may share a same overlapped region. In some embodiments, the third gantry 1212 may rotate relative to the second gantry 222, which is similar to that the first gantry 212 rotates relative to the second gantry 222.

Figure 11:
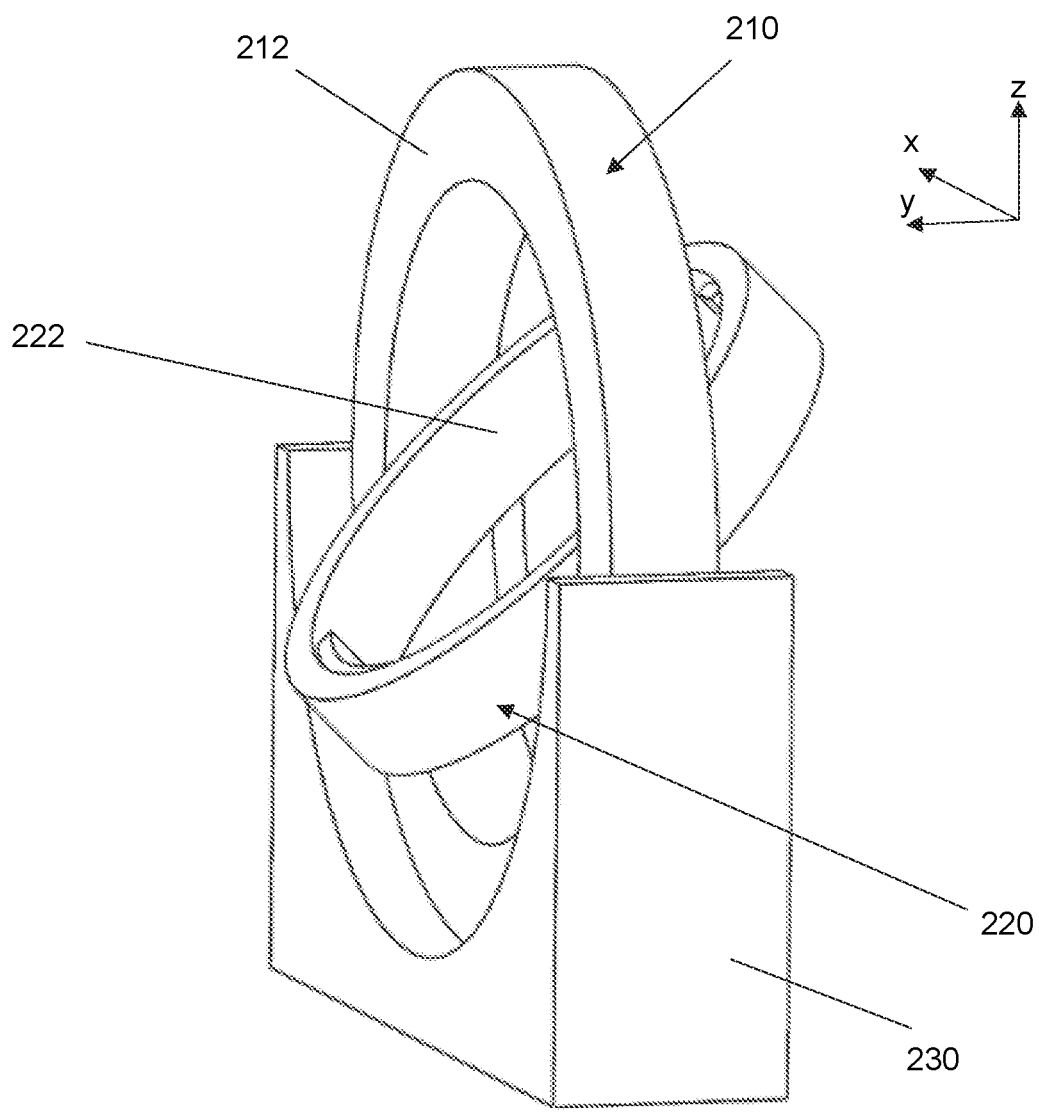
FIG. 11 is a schematic diagram illustrating another exemplary rotation state of the radiation device according to some embodiment of the present disclosure.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, at least one of the first gantry 212 and the second gantry 222 may be fixed and cannot rotate. For example, the second gantry 222 may be fixed and cannot rotate, while the first gantry 212 can rotate. As another example, as shown in FIG. 11, the first gantry 212 may be fixed and cannot rotate while the second gantry 222 can rotate. In some embodiments, the first medical device 211 and the second medical device 221 may both be imaging devices for performing multi-modality imaging on the object. In some embodiments, as shown in FIG. 11, the first device 210 and the second device 220 may be reversely arranged which is different from that illustrated in FIG. 2. That is, at least a portion of the second gantry 222 may be configured to be positioned within the first bore defined by the first gantry 212 and the second gantry 222 may rotate relative to the first gantry 212. For example, the first medical device 211 may define a second cylindrical accommodation space. The second medical device 221 may include a ring gantry. The second medical device 221 may be positioned within the second cylindrical accommodation space when the first medical device 211 and the second medical device 221 are at the initial position without rotation. Details of the first device 210 and the second device 220 arranged reversely may be similar to that of the first device 210 and the second device 220 as illustrated in FIG. 2.

Figure 5:
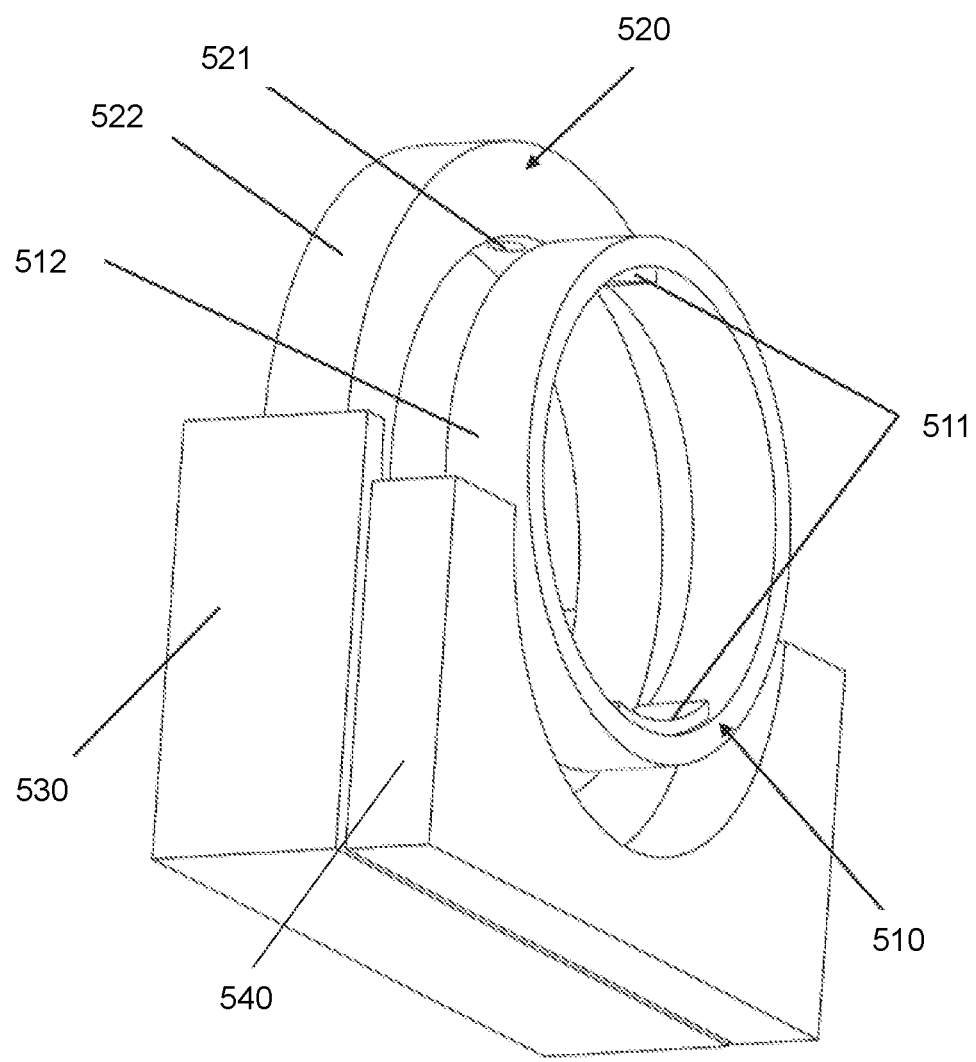
FIG. 5 is a schematic diagram illustrating an exemplary radiation device according to some embodiments of the present disclosure.

FIG. 5 is a schematic diagram illustrating an exemplary radiation device according to some embodiments of the present disclosure. The radiation device 500 provides an exemplary embodiment of the radiation device 110 as described in connection with FIG. 1. The radiation device 500 may include a first device 510, a second device 520, a support 530, and a support 540. As shown in FIG. 5, the first device 510 and the second device 520 may be at their initial positions. The coordinate system illustrated in FIG. 5 may be the same as that illustrated in FIG. 1. For illustration purposes, the following descriptions of the radiation device 500 being an IGRT device may not be intended to limit the scope of the present disclosure.

Figure 6:
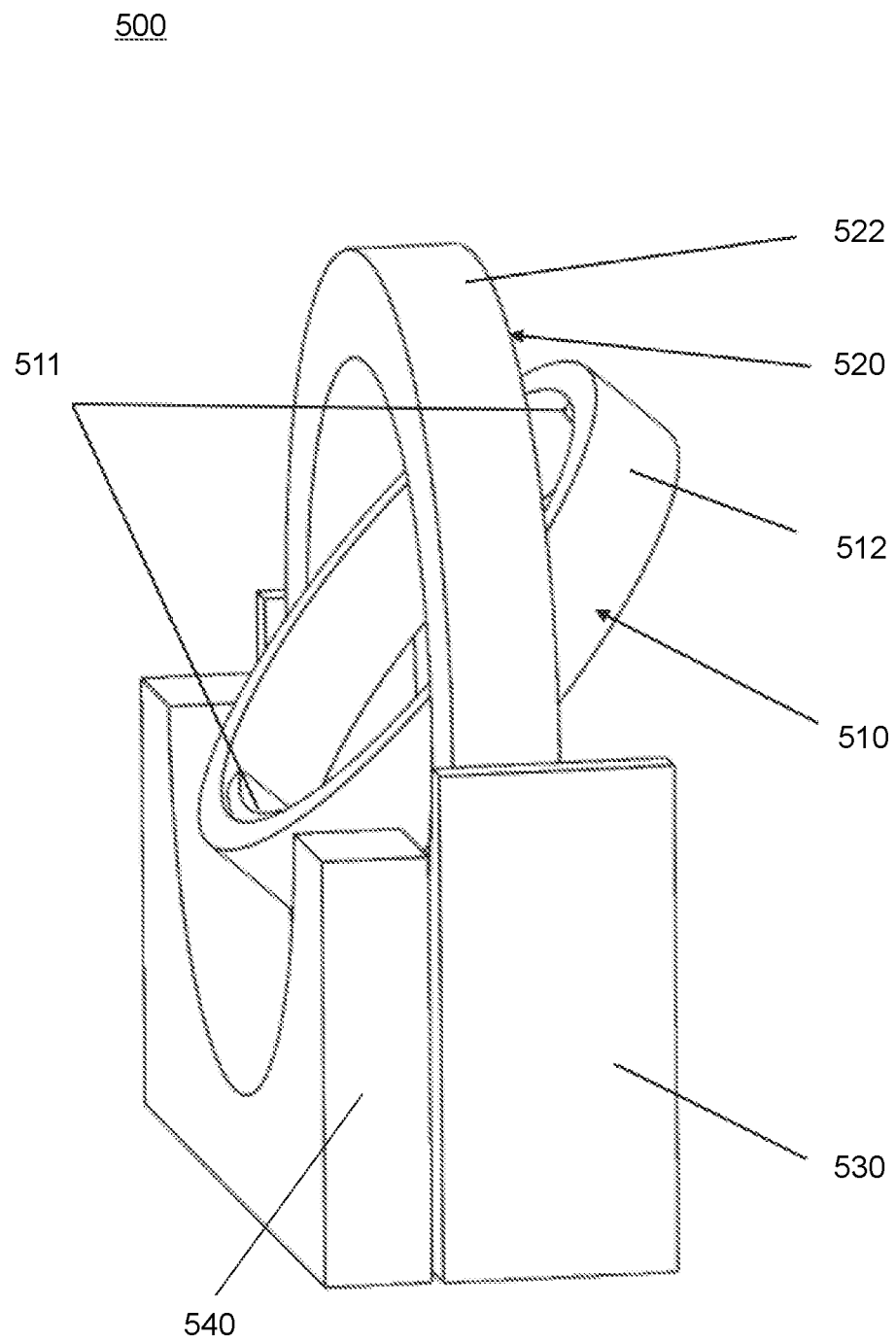
FIG. 6 is a schematic diagram illustrating an exemplary rotation state of the radiation device 500 according to some embodiments of the present disclosure.

The first device 510, the second device 520, and the support 530 may be similar to the first device 210, the second device 220, and the support 230, respectively, except that position configurations are different. The first device 510 may include a first medical device 511 (e.g., for imaging) operably coupled to or mounted on a first gantry 512. The second device 520 may include a second medical device 521 (e.g., for treatment) operably coupled to or mounted on a second gantry 522. When the first gantry 512 and the second gantry 522 are at their respective initial positions, the first gantry 512 and the second gantry 522 may be arranged in parallel and next to each other. The second gantry 522 may be operably coupled to or mounted to the support 530 and rotate relative to the support 530. The first gantry 512 may be operably coupled to or mounted to the support 540 and rotate relative to the support 540. At least a portion of the first gantry 512 may be configured to be positioned within a second bore defined by the second gantry 522 by rotating the first gantry 512. FIG. 6 is a schematic diagram illustrating an exemplary rotation state of the radiation device 500 according to some embodiments of the present disclosure. As shown in FIGS. 5 and 6, the first gantry 512 and the second gantry 522 may be ring gantries. At least a portion of the first gantry 512 may be positioned within a cylindrical accommodation space (i.e., the second bore) defined by the second gantry 522 when the first gantry 512 rotates from the initial position as shown in FIG. 5 to a third position as shown in FIG. 6. In such a configuration, compared with setting the first gantry 212 within the second gantry 222 as shown in FIG. 2, the setting of the first gantry 512 parallel to the second gantry 522 as shown in FIG. 5 may have less interference between the first gantry 512 and the second gantry 522. In comparison with the configuration illustrated in FIG. 2, the configuration illustrated in FIG. 5 may simplify the installation due to, e.g., the first gantry 512 and the second gantry 522 being installed on corresponding supports (e.g., the supports 530 and 540) individually with less interference. In addition, the first gantry 512 may not need to be positioned within the second bore defined by the second gantry 522, and the second bore defined by the second gantry 522 may be set to be relatively small in comparison with that of the second gantry 222. Accordingly, a height occupied by medical radiation system 100 (e.g., a height of the radiation device 500) may be reduced, which in turn may reduce a manufacturing cost of the medical radiation system 100.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the first gantry 512 and the second gantry 522 may be reversely arranged. That is, the first gantry 512 may be mounted on the support 530, and the second gantry 522 may be mounted on the support 540. In some embodiments, the first gantry 512 and/or the second gantry 522 may move along the y axis. For example, the first gantry 512 may move closely to or away from the second gantry 522 along the y axis.

FIG. 7 is a schematic diagram illustrating exemplary hardware and/or software components of a computing device on which the processing device 120 may be implemented according to some embodiments of the present disclosure. As illustrated in FIG. 7, the computing device 700 may include a processor 710, a storage 720, an input/output (I/O) 730, and a communication port 740.

The processor 710 may execute computer instructions (program code) and perform functions of the processing device 120 in accordance with techniques described herein. The computer instructions may include routines, programs, objects, components, signals, data structures, procedures, modules, and functions, which perform particular functions described herein. For example, the processor 710 may process data obtained from the radiation device 110, the terminal 140, the storage device 130, or any other component of the medical radiation system 100. In some embodiments, the processor 710 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 700. However, it should be note that the computing device 700 in the present disclosure may also include multiple processors, thus operations and/or method steps that are performed by one process 800 or as described in the present disclosure may also be jointly or separately performed by the multiple processors. For example, if in the present disclosure the processor of the computing device 700 executes both step A and step B, it should be understood that step A and step B may also be performed by two different processors jointly or separately in the computing device 700 (e.g., a first processor executes step A and a second processor executes step B, or the first and second processors jointly execute steps A and B).

The storage 720 may store data/information obtained from the radiation device 110, the terminal 140, the storage device 130, or any other component of the medical radiation system 100. In some embodiments, the storage 720 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 720 may store one or more programs and/or instructions to perform exemplary methods described in the present disclosure.

The I/O 730 may input or output signals, data, or information. In some embodiments, the I/O 730 may enable a user interaction with the processing device 120. For example, the processing device may display an image through the I/O 730. In some embodiments, the I/O 730 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 740 may be connected to a network (e.g., the network 150) to facilitate data communications. The communication port 740 may establish connections between the processing device 120 and the radiation device 110, the terminal 140, or the storage device 130. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 740 may be a standardized communication port, such as RS232, RS485, etc. In some embodiments, the communication port 740 may be a specially designed communication port. For example, the communication port 740 may be designed in accordance with the digital imaging and communications in medicine (DICOM) protocol.

Figure 8:
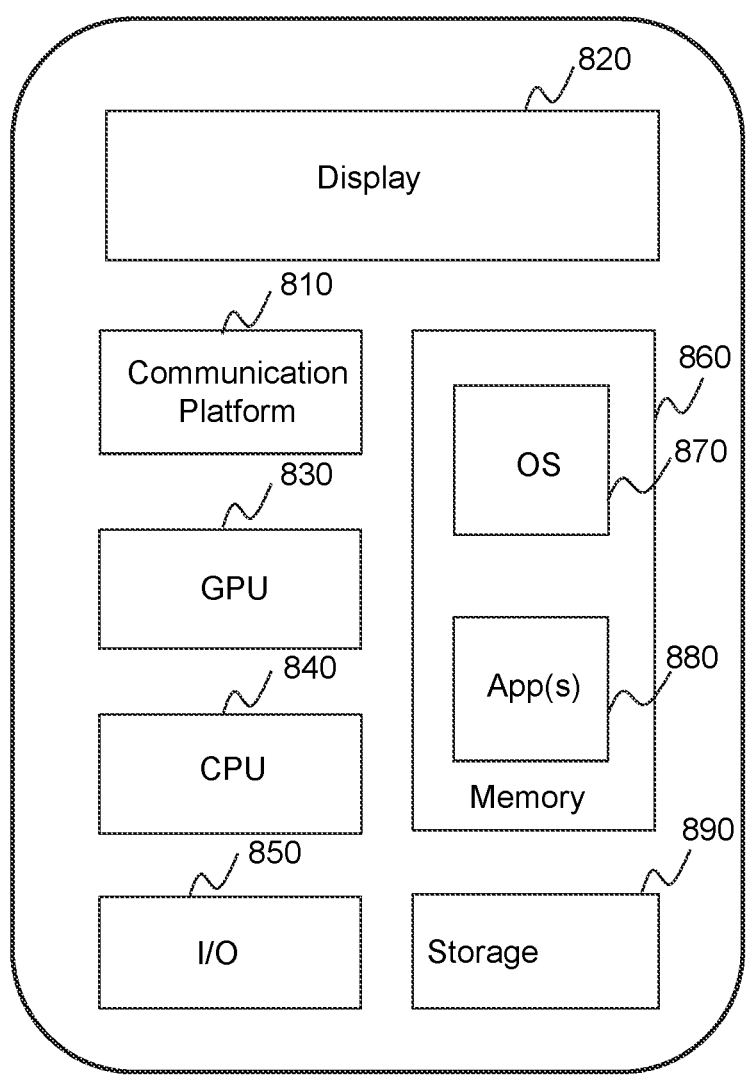
FIG. 8 is a schematic diagram illustrating exemplary hardware and/or software components of a mobile device on which the terminal 140 may be implemented according to some embodiments of the present disclosure.

FIG. 8 is a schematic diagram illustrating exemplary hardware and/or software components of a mobile device on which the terminal 140 may be implemented according to some embodiments of the present disclosure. As illustrated in FIG. 8, the mobile device 800 may include a communication platform 810, a display 820, a graphics processing unit (GPU) 830, a central processing unit (CPU) 840, an I/O 850, a memory 860, and a storage 890. In some embodiments, any other suitable component, including but not limited to a system bus or a controller (not shown), may also be included in the mobile device 800. In some embodiments, a mobile operating system 870 (e.g., iOS, Android, Windows Phone, etc.) and one or more applications 880 may be loaded into the memory 860 from the storage 890 in order to be executed by the CPU 840. The applications 880 may include a browser or any other suitable mobile apps for receiving and rendering information relating to image processing or other information from the processing device 120. User interactions with the information stream may be achieved via the I/O 850 and provided to the processing device 120 and/or other components of the medical radiation system 100 via the network 150.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 9:
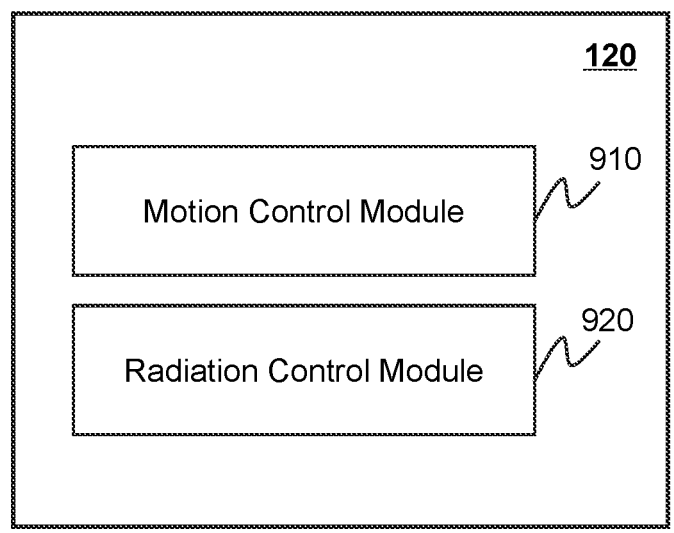
FIG. 9 is a block diagram illustrating an exemplary processing device according to some embodiments of the present disclosure.

FIG. 9 is a block diagram illustrating an exemplary processing device according to some embodiments of the present disclosure. As shown in FIG. 9, the processing device 120 may include a motion control module 910 and a radiation control module 920.

The motion control module 910 may be configured to cause one or more components of the medical radiation system to move and/or rotate. For example, the motion control module 910 may cause a table (e.g., the table 115) to move to a target position. The target position refers to a treatment position or an imaging position where the object may be treated and/or imaged. As another example, the motion control module 910 may be cause a first gantry (e.g., the first gantry 212) to rotate relative to a second gantry (e.g. the second gantry 222). As another example, the motion control module 920 may cause the second gantry 222 to rotate relative to the first gantry. More descriptions regarding the rotation of the first gantry and/or the rotation of the second gantry may be found elsewhere in the present disclosure (e.g., FIGS. 2-8, operation 1010 and the descriptions thereof).

The radiation control module 920 may be configured to cause one or more components of a radiation device (e.g., the radiation device 110, the radiation device 200, or the radiation device 500) to deliver radiation beams toward an object Imaging and/or treatment operation may be performed on the object using the delivered radiation beams. For example, the radiation control module 920 may cause a first medical device (e.g., the first medical device 211) of the radiation device to deliver radiation beams toward the object for performing a first operation on a first region of the object. As another example, the radiation control module 920 may cause a second medical device (e.g., the second medical device 221) of the radiation device to deliver radiation beams toward the object for performing a second operation on a second region of the object. In some embodiments, the first operation and the second operation may be performed synchronously or in order. For example, the first operation may be performed before, when, or after the second operation is performed. More descriptions regarding the causing the first medical device and/or the second medical device to perform corresponding operations may be found elsewhere in the present disclosure (e.g., operation 1020 and the description thereof).

In some embodiments, the processing device 120 may include a reconstruction module (not shown) configured to generate an image based on image data acquired in the first operation and/or the second operation. For example, the reconstruction module may acquire the image data (e.g., projection data) relating to the object. The reconstruction module may generate the image based on the image data using a reconstruction algorithm. More descriptions regarding the reconstruction process may be found elsewhere in the present disclosure (e.g., 1020 and the description thereof).

The modules in the processing device 120 may be connected to or communicate with each other via a wired connection or a wireless connection. The wired connection may include a metal cable, an optical cable, a hybrid cable, or the like, or any combination thereof. The wireless connection may include a Local Area Network (LAN), a Wide Area Network (WAN), a Bluetooth, a ZigBee, a Near Field Communication (NFC), or the like, or any combination thereof. Two or more of the modules may be combined as a single module, and any one of the modules may be divided to two or more units.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 120 may further include a storage module (not shown in FIG. 9). The storage module may be configured to store data generated during any process performed by any component of in the processing device 120. As another example, each of components of the processing device 120 may include a storage apparatus. Additionally or alternatively, the components of the processing device 120 may share a common storage apparatus. In some embodiments, one or more modules in the processing device 120 may be divided into two or more units. For example, the motion control module 910 may include a first motion control unit and a second control unit. The first rotation control unit may be configured to perform the function of rotating the first gantry (e.g., the first gantry 212 or the first gantry 512). The second motion control unit may be configured to perform the function of rotating the second gantry (e.g., the second gantry 222 or the second gantry 522). As another example, the radiation control module 920 may include two radiation control units. One of the radiation control units may be configured to control the first medical device (e.g., the first medical device 211 or the first medical device 511) emitting imaging beams. The other of the radiation control units may be configured to control the second medical device (e.g., the second medical device 221 or the second medical device 521) emitting treatment beams.

FIG. 10 is a flowchart illustrating an exemplary process for using a medical system according to some embodiments of the present disclosure. The process 1000 may be implemented in the medical radiation system 100 illustrated in FIG. 1. For example, the process 1000 may be stored in the storage device 130 and/or the storage 720 in the form of instructions (e.g., an application), and invoked and/or executed by the processing device 120 (e.g., the processor 710 illustrated in FIG. 7, or one or more modules in the processing device 120 illustrated in FIG. 9). The operations of the illustrated process presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting. For illustration purposes, the process 1000 may be described in connection with the radiation device 200 being an IGRT device of the medical radiation system 100. As described in FIG. 3, the radiation device 200 may include a first gantry 212 on which a first medical device 211 is mounted and a second gantry 222 on which a second medical device 221 is mounted. The first medical device 211 (e.g., an imaging device) may be configured to perform a first operation (e.g., an imaging operation) on a first region of an object. The second medical device 221 (e.g., a treatment device) may be configured to perform a second operation (e.g., a treatment operation) on a second region of the object. The first gantry 212 may be within a second bore defined by the second gantry 222 when the first gantry 212 and the second gantry 222 are at the initial position without rotation.

In 1010, the processing device 120 (e.g., the motion control module 910) may cause the second gantry 222 to rotate relative to the first gantry 212 such that the second region at least partially overlaps the first region.

In some embodiments, the processing device 120 may cause a table (e.g., the table 115) on which the object is placed to move to a target position. The target position may also be referred to as a treatment position or an imaging position where the object may be treated and/or imaged. When the object is at the target position, the processing device 120 may cause at least one of the second gantry 222 and the first gantry 212 to rotate, such that the second region at least partially overlaps the first region. For example, the processing device 120 may adjust an angle between the first gantry 212 and the second gantry 222 by rotating the first gantry 212 from the initial position to a first position and/or rotating the second gantry 222 from the initial position to a second position. Accordingly, a relative position between the first medical device 211 and the second medical device 221 may be adjusted to reduce interference between the first medical device 211 and the second medical device 221, thereby reducing or avoiding imaging beams from the first medical device 211 from interfering with treatment beams from the second medical device 221 to ensure a stable working state of the medical radiation system 100.

In 1020, the processing device 120 (e.g., the radiation control module 920) may cause the first medical device to perform the first operation and the second medical device to perform the second operation synchronously.

In some embodiments, the processing device 120 may cause the radiation source of the first medical device 211 to deliver imaging beams to the object while the second medical device 221 is delivering a treatment beam to the object. The detector of the first medical device 211 may detect at least a portion of the imaging beams. The processing device 120 may acquire image data (e.g., projection data) based on the detected imaging beams. The processing device 120 may generate an image based on the acquired image data, which can be used for guiding the positioning of the target volume. In some embodiments, the processing device 120 may reconstruct the image using a reconstruction algorithm. The reconstruction algorithm may include an iterative reconstruction algorithm (e.g., a statistical reconstruction algorithm), a Fourier slice theorem algorithm, a filtered back projection (FBP) algorithm, a fan-beam reconstruction algorithm, an analytic reconstruction algorithm, or the like, or any combination thereof. In some embodiments, the processing device 120 may cause the radiation source of the first medical device 211 to move and deliver the imaging beams when the treatment beam is on or off. For example, the processing device 120 may cause the radiation source of the first medical device 211 to deliver the imaging beams before, when or after the treatment operation is performed.

In some embodiments, the treatment beam delivered in 1020 may be delivered to a target volume inside the object to perform radiotherapy on the target volume. In some embodiments, the position of the target volume may change with time due to various motions, for example, cardiac motion (and its effect on other organs), respiratory motion (of the lungs and/or the diaphragm, and its effect on other organs), blood flow and motion induced by vascular pulsation, muscles contracting and relaxing, secretory activity of the pancreas, or the like, or any combination thereof. The image generated in 1020 may be used to monitor the position and/or the motion of the target volume during the radiotherapy.

In some embodiments, the processing device 120 may determine, based on the images, whether any change or adjustment is needed with respect to a treatment plan of the radiotherapy. In some embodiments, when detecting a movement or change of the target volume, the processing device 120 may revise the delivery of the treatment beam or the position of the object. For example, the processing device 120 may pause the delivery of the treatment beam, and then adjust the treatment head of the second medical device 221 to target at the position of the moved or changed target volume. As another example, the processing device 120 may pause the delivery of the treatment beam, and then adjust the position of the target volume with respect to the treatment beam to make the treatment beam target at the target volume. After the delivery of the treatment beam or the position of the object is adjusted, the treatment head of the second medical device 221 may resume the delivery of the treatment beam. In some embodiments, when detecting the movement or change of the target volume, the treatment head of the second medical device 221 may terminate the delivery. In some embodiments, the processing device 120 may generate a notification based on the detected movement or change of the target volume. In some embodiments, the notification may include information of the movement or change of the target volume. The notification may be in a form of text, video, audio, etc.

According to the systems and methods described in the present disclosure, during radiotherapy on a target volume, the processing device 120 may automatically generate and/or analyze images to record the radiotherapy, monitor the position of the target volume, assess the change of the position of the target volume, and/or determine how to proceed further with a treatment plan of the radiotherapy (e.g., to continue the radiotherapy as planned, to continue the radiotherapy with a revised plan, or to terminate the radiotherapy, etc.). In some embodiments, the monitoring, assessment, and/or adjustment may be performed semi-automatically with the input of a user (e.g., a doctor). For instance, the processing device 120 may transmit the images to be presented on the terminal 140 (e.g., a display) so that the user may analyze the images and provide an instruction as to how to proceed further with the treatment plan (e.g., to continue the radiotherapy as planned, to continue the radiotherapy with a revised plan, or to terminate the radiotherapy, etc.). As another example, the processing device 120 may first analyze the images and determine if any change occurs in the target volume and how much the change is. The processing device 120 may determine accordingly if any adjustment in the treatment plan is needed. If the change of the target volume or the adjustment needed in the treatment plan is within a threshold, the processing device 120 may adjust automatically. In some embodiments, a notification may be generated when the processing device 120 makes such a determination. If the change of the target volume or the adjustment needed in the treatment plan is not within a threshold, the processing device 120 may generate a notification to, e.g., the user to seek instructions from the user as to how to proceed further.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, when the first medical device 211 and the second medical device are imaging devices with different types, the two imaging devices may be configured to perform imaging operations on the object synchronously, which can improve imaging efficiency and provide clear and comprehensive images relating to the object for improving diagnostic accuracy.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A medical system, comprising:
   a first medical device mounted on a first gantry, the first medical device being configured to perform a first operation on a first region of an object; and
   a second medical device mounted on a second gantry, the second medical device being configured to perform a second operation on a second region of the object, wherein
      the second gantry rotates relative to the first gantry;
      the first gantry or the second gantry rotates around at least two orthogonal axes; and
      the first region at least partially overlaps the second region.

2. The medical system of claim 1, wherein the first medical device is an imaging device, and the first operation includes an imaging operation.

3. The medical system of claim 1, wherein the second medical device is a treatment device, and the second operation includes a treatment operation.

4. The medical system of claim 3, wherein the treatment device is a linear accelerator.

5. The medical system of claim 1, wherein the second medical device is a second imaging device, and the second operation includes a second imaging operation.

6. The medical system of claim 1, wherein the second gantry is a second ring gantry, and at least a portion of the second gantry is located within a first bore defined by the first gantry.

7. The medical system of claim 6, wherein the second gantry rotates around a central axis of the second gantry and a diameter of the second gantry.

8. The medical system of claim 1, wherein the first gantry is a ring gantry, and at least a portion of the first gantry is located within a second bore defined by the second gantry.

9. The medical system of claim 8, wherein the first gantry rotates relative to the second gantry, the first gantry rotating around a central axis of the first gantry or a diameter of the first gantry.

10. The medical system of claim 1, wherein the first gantry is movably connected to the second gantry.

11. The medical system of claim 1, wherein the first gantry and the second gantry are concentric, an isocenter of the first gantry coinciding with an isocenter of the second gantry.

12. The medical system of claim 1, wherein the first gantry and the second gantry are coaxial, the first gantry sharing a same axis with the second gantry.

13. The medical system of claim 1, wherein at least a portion of the first gantry is configured to be positioned within a second bore defined by the second gantry by rotating the first gantry.

14. The medical system of claim 1, further comprising a third medical device mounted on a third gantry, wherein
   the third medical device is configured to perform a third operation on a third region of the object,
   the third gantry rotates relative to the second gantry, and
   the third region at least partially overlaps the second region.

15. The medical system of claim 14, wherein the third medical device is a third imaging device, and the third operation includes a third imaging operation.

16. The medical system of claim 14, wherein the first region, the second region, and the third region share a same overlapped region.

17. The medical system of claim 1, further comprising a support on which the second gantry is mounted, and the second gantry rotates relative to the support.

18. A method for using a medical system including a first medical device and a second medical device, implemented on a computing device including at least one processor and at least one storage device, wherein the first medical device is configured to perform a first operation on a first region of an object and the second medical device is configured to perform a second operation on a second region of the object, the method comprising:
   causing a second gantry on which the second medical device is mounted to rotate relative to a first gantry on which the first medical device is mounted such that the second region at least partially overlaps the first region, wherein the first gantry or the second gantry rotates around at least two orthogonal axes; and
   causing the first medical device to perform the first operation and the second medical device to perform the second operation synchronously.

19. The method of claim 18, wherein the first medical device is an imaging device and the second medical device is a treatment device.

20. The method of claim 18, wherein the first medical device is an imaging device and the second medical device is a second imaging device.

\* \* \* \* \*